Figure 1:
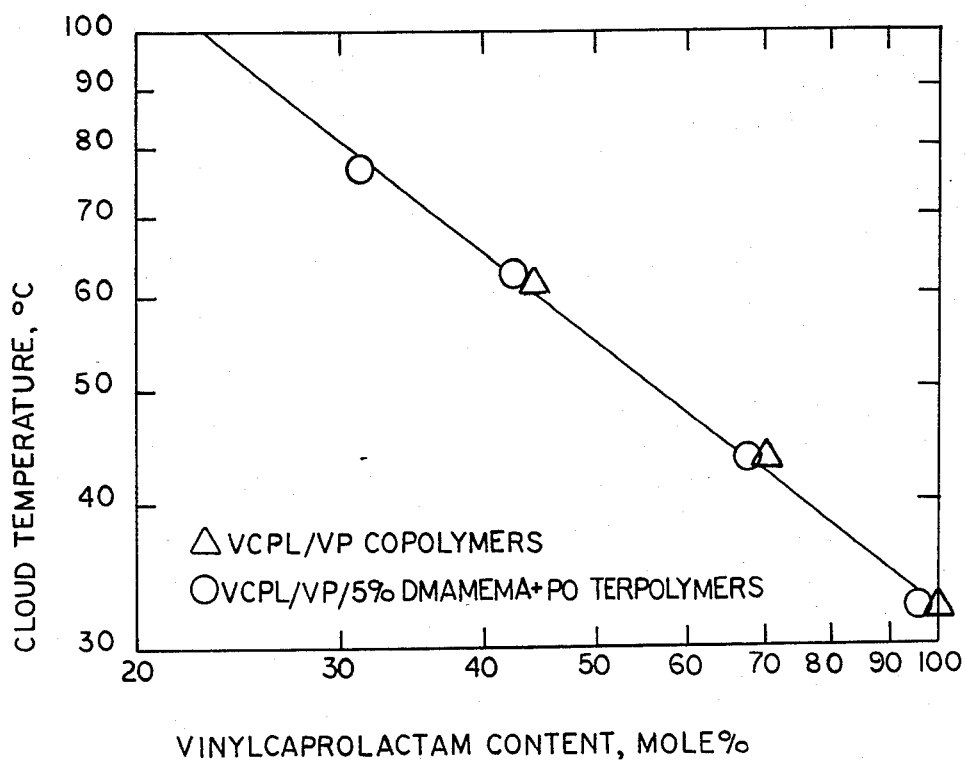

United States Patent [19]

Lorenz et al.

[11] Patent Number: 4,521,404
[45] Date of Patent: Jun. 4, 1985

[54] POLYMERIC HAIR PREPARATION

[75] Inventors: Donald H. Lorenz, Basking Ridge; Edward J. Murphy, Wayne; John M. Rutherford, Jr., Kinnelon, all of N.J.

[73] Assignee: GAF Corporation, Wayne, N.J.

[21] Appl. No.: 440,648

[22] Filed: Nov. 10, 1982

Related U.S. Application Data

[63] Continuation-in-part of Ser. No. 292,329, Aug. 13, 1981, abandoned.

[51] Int. Cl.³ .......................... A61K 7/09; A45D 7/00; C08F 226/10
[52] U.S. Cl. ........................ 424/71; 424/70; 424/47; 424/81; 132/7; 526/264
[58] Field of Search ............ 424/71, 70, 81, 47; 132/7; 526/264

[56] References Cited

U.S. PATENT DOCUMENTS

| 3,145,147 | 8/1964 | Glickman | 424/47 |
| 3,862,091 | 1/1975 | Barabas et al. | 526/264 |
| 3,933,766 | 1/1976 | Hoffmann et al. | 526/264 |
| 3,954,960 | 5/1976 | Valan | 424/47 |
| 4,223,009 | 9/1980 | Chakrabarti | 424/47 |

Primary Examiner—Sidney Marantz
Assistant Examiner—Shawn P. Foley
Attorney, Agent, or Firm—Marilyn J. Maue; Joshua J. Ward

[57] ABSTRACT

The present invention relates to a polymeric hair conditioning composition of vinyl pyrrolidone monomer, an ammonium derivative monomer and a substantially major amount, based on said monomers, of vinyl caprolactam said polymeric composition optionally containing a minor amount of stearyl methacrylate. Suitable ammonium derivative monomers include dimethylamino propyl methacrylamide, dimethyl diallyl ammonium chloride and a dialkylamino alkyl methacrylate, such as for example dimethylamino ethyl methacrylate.

10 Claims, 1 Drawing Figure

EFFECT OF VINYLCAPROLACTAM CONTENT
ON COPOLYMER CLOUD TEMPERATURE

EFFECT OF VINYLCAPROLACTAM CONTENT
ON COPOLYMER CLOUD TEMPERATURE

POLYMERIC HAIR PREPARATION

This application is a continuation-in-part of Ser. No. 292,329, filed Aug. 13, 1981, now abandoned.

This invention relates to terpolymers and tetrapolymers and to cosmetic preparations and especially to hair setting and conditioning compositions containing certain polymers of vinyl caprolactam, vinyl pyrrolidone, and an ammonium derivative containing monomer of 6 to 12 carbon atoms such as a dialkylamino alkyl methacrylate or acrylate, a dialkyl dialkenyl ammonium halide or a dialkylamino alkyl methacrylamide.

BRIEF DESCRIPTION OF THE PRIOR ART

In the field of hair care, setting, waving, conditioning and the like, several broad types of hair treating preparations have been proposed, the principal ones being cationic surfactants, superfatting materials, water soluble proteins and synthetic polymers, in a suitable cosmetically acceptable medium. The synthetic polymer-containing preparations are generally regarded as most effective, particularly those containing water soluble cationic polymers which are substantive to hair and exhaust thereon from solution or diluent medium. British Pat. No. 1,331,819 and U.S. Pat. Nos. 3,910,862, 3,914,403, 3,954,960 and 4,057,533, the disclosures of which are incorporated herein, describe water soluble cationic quarternized polymers of vinyl pyrrolidone (N-vinyl-2-pyrrolidone), hereafter referred to as VP and a dialkylamino alkyl acrylate or methacrylate, which have been found to be highly effective in providing most of the properties considered necessary in the theoretically perfect hair preparation, as in fact also described in said patents. The hair preparations described in said patents are however wanting in certain respects, as for example cost of producing the quarternized copolymers, and a curl retention under high humidity conditions, an ease of removability and/or a resistance of build-up not as high as could be desired.

U.S. Pat. No. 4,223,009 attempts to provide an improved system through the use of a copolymer of 99.5 to 45.1 mole percent vinyl pyrrolidone, 0.5 to 4.9% of an acrylate and 0 to 50% of an ethylenically unsaturated copolymerizable monomer such as the alkyl vinyl ethers, e.g. the methyl, ethyl, octyl and lauryl vinyl ethers; acrylic and methacrylic acid and esters thereof, e.g. methyl acrylate, ethyl acrylate and methyl methacrylate; vinyl aromatic monomers, e.g. styrene and alpha-methyl styrene; vinyl acetate and chloride; vinylidene chloride; acrylonitrile and methacrylonitrile and substituted derivatives thereof; acrylamide and methacrylamide and N-substituted derivatives thereof; crotonic acid and esters thereof, e.g. methyl and ethyl crotonate; and the like.

The patent broadly defines the acrylate as being a monomer of the formula

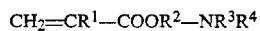

$$CH_2=CR^1-COOR^2-NR^3R^4$$

wherein
R$^1$ is H or CH$_3$,
R$^2$ is C$_{1-20}$ alkenyl, and
R$^3$ and R$^4$ are independently C$_{1-4}$ alkyl.

U.S. Pat. No. 4,223,009 further indicates that it was highly surprising to discover that elimination of the quarternization step required in accordance with the teachings of said patents not only did not result in any significant detriment to the properties of the hair preparations containing such polymers, but proved advantageous in substantially reducing the costs of manufacture and in providing hair preparations yielding improved properties in the treated hair with respect to improved curl retention under high humidity conditions, ease of removability and/or resistance to build-up with repeated use, among other miscellaneous advantages.

The shortcomings of the use of poly-N-vinyl-2-pyrrolidone (PVP) in hair conditioning formulations is expounded upon in U.S. Pat. No. 3,145,147. According to the patent, current popular aerosol hair spray compositions contain as the hair setting and waving medium, poly-N-vinyl-pyrrolidone (PVP). When a PVP-alcohol solution is applied in an aerosol system to human hair under a relative humidity of less than 50%, the tendency of the resulting film to tackiness is minimal. As a result thereof, the preparation is acceptable by all consumers. However, when the relative humidity is above 50%, and particularly in humid atmospheres, films of PVP obtained by spraying from an aerosol system, pick up considerable moisture. The moisture is retained and results in a tacky film. In view of this property of moisture retention, these aerosol preparations are extremely undesirable where a dry hair condition is required as in the case with most users. The equilibrium water content of PVP depends upon the relative humidity of the atmosphere. The moisture content varies in a linear fashion with relative humidity, and the equilibrium percentage of moisture is about one-third of the relative humidity. Thus if PVP is exposed to a relative humidity of 50%, the moisture pick-up is approximately one-third of the relative humidity, and therefore the resulting film contains about 13-14% moisture. To overcome the unique hygroscopicity of PVP, it has been suggested in the cosmetic art to employ detackifying agents such as shellac, cellulose acetate-propionate, etc. The former yields films which become opaque at high humidities, and the latter yields films which are insoluble to ethyl alcohol. Carboxymethyl cellulose, celluloseacetate, methyl methacrylate polymer, polyvinyl formal, etc. are not effective as detackifiers under conditions of extremely high humidities.

Another drawback of PVP is that in the course of its manufacture and handling, the polymer picks up sufficient moisture (water from the atmosphere) to substantially modify its solubility in solvents, other than lower alcohols, such as acetone, methylene chloride, etc. and prohibits its use in formulation of aerosol propellent mixtures. However, storage of PVP at 50% relative humidity yields a material which possesses solubility at a 10% level in absolute ethanol but is not completely soluble in acetone and methylene chloride. One prime reason which rules out the use of PVP in the formulation of aerosol compositions for the application of films to surfaces other than hair is its insolubility or rather insufficient solubility in acetone and methylene chloride. In the formulation of protective film coatings for surfaces such as silver and silver plate ware to protect them from tarnishing, etc., coupled with fast drying, a concentration of the film forming medium must be at least 5% and usually the preferred concentration being 10% and higher.

In order to provide a formulation which does not have the shortcomings of PVP systems, U.S. Pat. No. 3,145,147 advocates the use of copolymers of N-vinyl-ε-caprolactam. The patent discloses that the copolymerizable compounds which may be copolymerized with N-vinyl-ε-caprolactam include vinyl esters such as vinyl acetate, vinyl isopropenyl acetate and the like; alkyl acrylates such as methyl acrylate, ethyl acrylate, methyl methacrylate and the like; acrylamides such as acrylamide, methacrylamide and the like; acrylonitriles such as acrylonitrile, methacrylonitrile and the like; alkyl vinyl ethers such as methyl vinyl ether, ethyl vinyl ether, isopropenyl methyl vinyl ether and the like.

Generally, the above mentioned U.S. patent demonstrates the greater water sensitivity of vinyl pyrrolidone polymers over that of vinyl caprolactam polymers.

THE INVENTION

The present invention provides a hair conditioning composition consisting of or containing a terpolymer derived from vinyl pyrrolidone monomer, an ammonium derivative monomer and a substantially major amount, based on said monomers, of N-vinyl-ε-caprolactam.

The polymeric composition may optionally contain a minor amount of a fourth monomer such as stearyl methacrylate. Performance qualities of a hair preparation polymer are frequently modified by the use of additives to the hair preparation solution. Alternatively, the polymer may be modified for a given attribute. For example, the smooth and effortless combining of hair, treated with a hair preparation polymer, may be effected by the incorporation of small amounts of stearyl methacrylate into the polymer backbone. Similarly, other specific attributes may be modified or built into the polymer by incorporation of other monomers. Such attributes may be improved solubility, static resistance, ultraviolet protection, etc. or other functions which do not alter the basic high performance of the present terpolymer. When additional modifying monomers are employed they are incorporated in minor amount preferably not more than 7 weight %, most preferably not more than 3 weight %.

Suitable ammonium derivative monomers having 6 to 12 carbon atoms include diallylamino alkyl methacrylamides, e.g. dimethylamino propyl methacrylamide, dialkyl dialkenyl ammonium halides, e.g. dimethyl diallyl ammonium chloride and a dialkylamino alkyl methacrylate or acrylate, e.g. dimethylamino ethyl methacrylate (DMAEMA). It has been found that polymers made from the above monomers can be used to produce surprisingly high quality, low cost hair conditioning products.

The polymers of the present invention preferably comprise 17–32 weight % N-vinyl pyrrolidone; 65–80 weight % vinyl-ε-caprolactam; 3–6 weight % ammonium derivative and 0–5 weight % stearyl methacrylate monomers. The polymers can be in the form of random, block or alternating structure having number average molecular weights ranging between about 20,000 and about 700,000; preferably between about 25,000 and about 500,000. The hair conditioning agents of this invention are regarded as N-vinyl-ε-caprolactam polymers containing 2 or 3 additional monomers.

These polymers are conveniently prepared by subjecting the above monomers, either in admixture or added sequentially into a reactor, to a temperature of between about 40° C. and about 120° C. under from about 10 psig. to about 150 psig. for a period of from about 0.5 to about 10 hours in the presence of a free radical polymerization catalyst, such as organic and inorganic peroxides, e.g. hydrogen peroxide, t-butyl peroxide or an azo compound e.g. azobisisobutyronitrile, 2,2'-azobis-(2,4-dimethyl valeronitrile) etc. The polymerization is beneficially effected with agitation in solution, suspension or emulsion wherein the reaction medium is alcohol, benzene, hexane, water or any mixture thereof. The polymeric product is separated and recovered by precipitation and filtration, distillation, decantation, evaporation of solvent or any other conventional method.

It is to be understood that other conventional methods of polymerization can be employed and will become apparent to those skilled in the art from the foregoing discussion of related patents.

We have found that terpolymers incorporating polyvinyl-ε-caprolactam and vinyl pyrrolidone monomers display a surprising synergistic behavior in withstanding high humidity holding failure. This has been established by testing hair samples treated with instant terpolymer at 90% relative humidity at 80° F. (27° C.).

Polyvinyl pyrrolidone is known to be a very hygroscopic resin; whereas polyvinyl-ε-caprolactam is much less so. The hygroscopicity of the former resin causes failure to retain hair curl under high humidity conditions. The polyvinyl-ε-caprolactam, being substantially less hygroscopic retains hair curl under these conditions. Thus, it was completely unexpected, that partial replacement of N-vinyl-ε-caprolactam (VCPL) by vinyl pyrrolidone (VP) results in an actual improvement in high humidity holding over VCPL alone. In fact, this effect increases as the VP was increased. However, the amount of VP incorporation is limited by the tackiness of the resin which occurred when significantly more than 28% by weight of the final polymer was vinyl pyrrolidone.

Another critical parameter is dependent upon resin build-up on the hair. In order to effect removal of the copolymer during shampooing usually at about 100° F. (38° C.)—it is very desirable to change the characteristics of polyvinyl-ε-caprolactam which becomes insoluble in water above 30° C. (86° F.). Unexpectedly, the incorporation of dimethylaminoethyl methacrylate (a highly water soluble monomer) did not change the cloud-clear point (temperature at which the N-vinyl-ε-caprolactam resin loses solubility). However, replacement of N-vinyl-ε-caprolactam by vinyl pyrrolidone does afford a significant change in cloud-clear point, and hence an improvement in shampooability.

As a preferred method for preparation of polymers involving VCPL, VP and DMAEMA the selected mixture of monomers is charged to a reactor containing a suitable solvent, e.g. 100–200 ml. of absolute ethanol, and the solution purged with nitrogen for between about 0.25–2 hrs., e.g. for about 0.5 hour. The purged solution is then heated to about 50°–75° C., e.g. to about 60° C., and a peroxy or azo type catalyst such as 2,2'-azobis(2,4-dimethyl valeronitrile) catalyst (e.g. 0.053 g. in 10 ml. of absolute ethanol) is added to initiate reaction. After several hours, (1–5 hours e.g. 2 hrs.) at reaction temperature, an additional amount of the catalyst (e.g. 0.070 g. in 10 ml. absolute ethanol) is introduced and the temperature in the reactor is raised by about 5–15 degrees where it is held until the reaction is completed, usually within about 2.5 hours. The reaction mixture is then refluxed and a third portion of the catalyst (e.g. 0.088 g. in absolute ethanol) is added. After refluxing for several hours, the reaction mixture is cooled to room temperature and the polymeric product recovered by evaporation of solvent. The polymers prepared in this way were then tested as hair conditioning agents.

It is to be understood that modifications in the above preparation of the present terpolymers, such as substitution of another free radical catalyst, variations in temperature and pressure, incremental or continuous catalyst addition and other conventional methods of product recovery can be used without departing from the scope of this invention.

Reference is now had to the accompanying examples which illustrate the benefits of the present terpolymer and tetrapolymer.

EXAMPLE 1

A series of VCPL/VP copolymers and VCPL/VP/5% DMAEMA+PO terpolymers were prepared according to the above procedure for the purpose of determining their cloud temperatures (i.e., the temperature above which they precipitate from aqueous solution), with the expectation that increasing the hydrophilicity of the resin should improve its shampooability. These data are shown in Table I, and when the cloud temperatures are plotted against VCPL content of the copolymers, they fall on a common line showing an inverse correlation in a log-log plot with an extrapolated 100° C. cloud temperature at about 23 mole percent VCPL, as shown in FIG. 1.

TABLE I

CLOUD TEMPERATURES OF
N—VINYL-ε-CAPROLACTAM POLYMERS[b]

| Polymer Composition, mole % | | | |
|---|---|---|---|
| VP | VCPL | DMAEMA + PO | Cloud Temperature[a] |
| 0 | 100 | 0 | 32.3° C. |
| 29.5 | 70.5 | 0 | 43.5 |
| 55.6 | 44.4 | 0 | 61.5 |
| 79 | 21 | 0 | >100 |
| 0 | 95.5 | 4.5 | 32.5 |
| 27.9 | 67.6 | 4.5 | 43.4 |
| 52.9 | 42.6 | 4.5 | 62.4 |
| 75.3 | 20.2 | 4.5 | >100 |
| 85.6 | 9.9 | 4.5 | >100 |

[a]Determined by diluting a 40% solution in ethanol with water to 5% and slowly heating with stirring on a hot plate until the polymer precipitated.
[b]Samples of VCPL/VP/DMAEMA were quaternized at times with either diethyl sulfate or propylene oxide (PO). No effect on hairholding or cloud temperature (in water) was detected by such modification. Thus the quaternized and unquaternized terpolymers provide equivalent performance.

It can be seen that incorporation of DMAEMA into VCPL did not increase the cloud temperature to any appreciable extent, but incorporation of VP did do so. However, the terpolymer containing a major portion of VP was tacky at a relative humidity above 50%.

All of the resins under evaluation had a 2.5% solids content which is the optimum level for the GANTREZ ES-225 ® resin. Surprisingly, the VCPL terpolymer exhibits a substantially better humidity holding power than GANTREZ ES-225 ® on an equal weight basis, and therefore, can be used at a decreased weight level without adversely affecting its humidity holding power.

EXAMPLE 2

Preparation of a Terpolymer of the Present Invention

Into a glass reactor containing 114 ml. of absolute ethanol was charged 49.7 g. VCPL, 16.8 g. of VP and 3.5 g. of DMAEMA. The reactants were purged with nitrogen and heated to 50° C. after which 0.053 g. of VAZO 52 (2,2'-azobis[2,4-dimethyl valeronitrile]) dissolved in 10 ml. of absolute ethanol was added and the reaction was maintained for two hours at 60° C. Another 0.070 g. of VAZO 52 dissolved in 10 ml. absolute ethanol was added at 70° C. and the reaction mixture held for two additional hours. The reaction was brought to reflux (78° C.) and an additional 0.088 g. of VAZO 52, dissolved in 10 ml. absolute ethanol, was added. After two hours at reflux the reaction was cooled to room temperature and recovered by evaporation of alcohol. The K value of the terpolymer produced was 45.0. (w/w at 1% concentration in absolute ethanol) which is equivalent to a number average molecular weight of about 50,000.

A series of 71/24/5 terpolymers of various molecular weights, produced by varying the initial temperature of reaction from 50°-70° C. (K value 30-60; MW 25,000-100,000) were synthesized in a similar manner. Testing of all of these polymers in a hydro-alcoholic hairspray formulation indicated that they were all at least as effective as GANTREZ ES-425 ®, but optimum results were obtained from the terpolymers having viscosity K values of from K 35 to K 50 (MW about 30,000-80,000).

EXAMPLE 3

To test hair curl humidity holding, hair tresses were treated with polymers of various VP and VCPL ratios at the 1.5% solids level in hydroalcoholic and anhydrous alcoholic systems. They were dried under ambient conditions and the height of curl above a reference point measured. The tresses were exposed to 90% relative humidity (R.H.) at 80° F. (27° C.) and the height of curl measured again after the elapse of various periods. The height which remains is expressed as a percentage of the original height.

Some significant results, showing the percentage curl retention after 45 minutes are shown in Table II.

TABLE II

| Polymer Composition** VP/VCPL/ DMAEMA | VP/VCPL Ratio | % curl retention* | | Tack |
|---|---|---|---|---|
| | | hydroalcoholic system | anhydrous alcoholic system | |
| 0/95/5 | 0/100 | 63 | 64 | No |
| 19/76/5 | 20/80 | 78 | 81 | No |
| 47.5/47.5/5 | 50/50 | 89 | 90 | High |

**Polymers were prepared by the method set forth in Example 2 except that the monomers in the proportions given in Table II were substituted for the monomers recited in Example 2.
*% curl retention measured after 45 minutes at 90% relative humidity (R.H.) and 80° F.

It was entirely contrary to expectation that going from 95/5 VCPL/DMAEMA polymer to 47.5/47.5/5 VP/VCPL/DMAEMA terpolymer would improve the resistance to high humidity holding fade due to the greater water sensitivity of VP over that of VCPL. As compared to the VP/VCPL/DMAEMA polymers herein described, VP/DMAEMA copolymer, devoid of VCPL, was markedly inferior in curl retention.

A tack test was designed where the product is sprayed on a glass plate, dried thoroughly, and then the plate is conditioned under constant temperature and humidity. Three cotton balls are gently laid on the film. At 20, 40 and 60 minutes, one of the balls is finger pressed onto the film and then removed. The amount of cotton left on the film is indication of tackiness. The butyl monoester of poly(methyl vinyl ether/maleic anhydride) of 50% solids in ethanol (GANTREZ ES-425) ® and the ethyl monoester of poly(methyl vinyl ether/maleic acid) of 50% solids in ethanol (GANTREZ ES-225) ® as well as PVP K-30, were used as controls. All of the N-vinyl caprolactam/VP terpolymers with VCPL content less than 60% showed tackiness quite similar to PVP K-30, (i.e. high tack). However, by increasing the VCPL content to 65% preferably to 71%, the system was equivalent to GANTREZ ES-425 ® (non tacky).

Two samples were evaluated for tackiness properties according to a tack test designated as ASTM # D 3121-73.

Films of each resin were cast on a glass plate, dried and placed in an environmental chamber. The humidity therein was gradually increased to the point when bead travel distance was interrupted due to tackiness of the film.

A sample of VP/VCPL/DMAEMA terpolymer, in proportions 47.5/47.5/5.0, and having a K value of 46.1 became tacky at 96% R.H. and 80° F. (27° C.). The bead travel averaged 86 mm.

A sample in which the VP/VCPL/DMAEMA proportions were 21/74/5, having a K value of 40.8 remained dry. The shot bead rolled the entire length of the glass plate.

Touching the films with a finger also indicated the increased amount of tack of the first sample when compared with the non-tacky second sample.

EXAMPLE 4

Additional tests were similarly carried out on 47.5% VP/47.5% VCPL/5% DMAEMA terpolymers wherein a portion of the VCPL was replaced with more hydrophobic monomers, namely lauryl methacrylate (5%), stearyl methacrylate (5%) and vinyl acetate (10%). These experiments were carried out to test possible beneficial effects of incorporating a more hydrophobic monomer to reduce tackiness; however no substantial improvement over the original VP/VCPL/DMAEMA was found. The terpolymers of this example were prepared by the procedure set forth in Example 2.

The incorporation of a major amount of VCPL is essential in minimizing or eliminating tackiness in the terpolymer composition. This manifestation or reduced tackiness is unexpectedly due at least in part to interaction of VCPL with comonomers and not simply based on a balance of hydrophobic-hydrophilic properties.

The effect of molecular weight was also examined to determine a threshold molecular weight for optimum holding. Evaluation of these tests showed a high molecular weight (above a K value of 35) to improve holding.

Tests showed a polymer produced from 69–73/22–26/3–6 ratio of VCPL/VP/DMAEMA monomers produce a hairspray resin with hair holding properties at least equal in quality, and in most cases better than, the best resins in commercial use, such as GANTREZ ES-425 ® and GANTREZ ES-225 ®, and PVP homopolymer K-40 and PVCPL homopolymer K-40 while requiring approximately half the concentration level of these resins.

EXAMPLE 5

A tetrapolymer was synthesized by the procedure outlined in Example 2. The monomer charges consisted of vinyl caprolactam 47.95 g.; vinyl pyrrolidone 16.8 g.; DMAEMA 3.5 g.; and stearyl methacrylate 1.75 g. The reaction was initiated at 50° C. and azo bis (2,4-dimethyl valeronitrile) catalyst was added in increments as described in Example 2. After cooling to room temperature the K value (w/w) was determined at 1% in absolute alcohol and recorded as 38.1. The tetrapolymer product was then formulated into an anhydrous hairspray preparation and compared to the 71/24/5 (VCPL/VP/DMAEMA) polymer. The high humidity hair holding ability of the tetrapolymer was not diminished by the incorporation of the stearyl methacrylate, however the combing quality of the tetrapolymer showed improvement by virtue of a more effortless passage of the comb through the hair tresses.

The above procedure was repeated, except that tert-butyl peroxy pivilate catalyst was substituted for the above azo catalyst and the identical tetrapolymer was produced and had the same excellent hair holding and combability properties.

While the 71/24/5 VCPL/VP/DMAEMA resin is an excellent hair spray, the low cloud temperature of the polymer would be expected to detract from its use in hair conditioning resins for shampoo.

However, in a cream rinse of the following formulation and an anionic shampoo, the cloud points of the formulations incorporating this resin were found to be 50° and 70° C. respectively.

The creme rinse formulation consisted of:

|  | % |
|---|---|
| Triton X400 (stearyl dimethyl benzyl ammonium chloride) | 7.0 |
| Glyceryl monostearate | 2.0 |
| Cerophyl 28 (cetyl lactate) | 1.0 |
| Glutoraldehyde (25%) | .4 |
| Sodium hydroxide (10%) | .26 |
| VCPL/VP/DMAEMA* (38.12% solids) | 1.05 |
| H₂O (distilled) to 100% | |

An Amphoteric shampoo formulation suitable for the present terpolymer comprises:

|  | % |
|---|---|
| Gafac RS-610 (free acid of a complexed phosphonate ester) | 6.00 |
| Minranol cm. conc. (N.P.) (dicarboxylic coconut derivative of an imidazoline, sodium salt) | 25.00 |
| Distilled water | 58.03 |
| 10% citric acid solu. | 7.00 |
| PEG 6000 distearate (polyethylene glycol of MW 6000) | 1.00 |
| sodium sulfite | .10 |
| perfume | .25 |
| VCPL/VP/DMAEMA* | 2.62 |

The anionic shampoo formulation tested with the present terpolymer consisted of:

|  | % |
|---|---|
| Distilled H₂O | 53.58 |
| Sipon LT.6 (TEALS) (triethanolamine lauryl sulfate) | 35.00 |
| Monamid CMA (coconut monoethanolamine) | 3.00 |
| Coconut fatty acid | 2.00 |
| Triethanolamine | 1.40 |
| PE 6000 distearate | 1.40 |
| NaCl | .60 |
| Sodium Sulfite | .10 |
| perfume | 3.0 |
| VCPL/VP/DMAEMA* | 2.62 |

*71/24/5 ratio
PEG is polyethylene glycol

The following clear creme rinse formulation is also highly effective.

|  | % |
|---|---|
| Distilled water | 95.08 |

-continued

| | % |
|---|---|
| Natrosol 250 HHR (hydroxyethyl cellulose) | .40 |
| Ammonyx KP (ollyl dimethylbenzyl ammonium chloride) | 4.00 |
| VCPL/VP/DMAEMA* | .52 |

*71/24/5 ratio
PEG is polyethylene glycol

The foregoing formulations were comparable to those using a resin sold under the registered trademark GAFQUAT® and designated as GAFQUAT® 755 N, (the polymer of VP/DMAEMA of 20% solids in aqueous solution) supplied by GAF Corp. with respect to substantivity, curl retention, build-up and build-up removal.

The VCPL/VP/DMAEMA resin is free of carboxylic acid groups and accordingly minimizes corrosion problems of the type which would be encountered with a formulation of the type disclosed in U.S. Pat. No. 4,164,562 when used with the hydroalcohol solvents of the patent.

Although the polymer of the instant invention has, as its primary function in a formulation, the significant improvement in humidity holding, other beneficial properties can be realized through the use adjuvants or added monomers.

It is to be understood that the improved hair conditioning agents of this invention are also achieved when the other ammonium derivative monomers disclosed herein are substituted in the above examples of DMAEMA.

What is claimed is:

1. In a hair conditioning composition containing a polymer, said polymer derived from polymerization of vinyl pyrrolidone and an ammonium derivative monomer having from 6 to 12 carbon atoms selected from the group consisting of dialkylaminoalkyl methacrylamide, dialkyl dialkenyl ammonium halide and a dialkylamino alkyl methacrylate or acrylate, wherein the improvement comprises incorporating therein a substantially major amount, based on said monomers, of N-vinyl-ε-caprolactam monomer to provide a hair conditioning agent having a number average molecular weight between about 20,000 and about 700,000.

2. The hair conditioning composition of claim 1 further comprising a surfactant.

3. A hair conditioning polymer comprising between about 17–32 weight % N-vinyl pyrrolidone, between about 65–80 weight % N-vinyl-ε-caprolactam, between about 3–6 weight % of an ammonium derivative monomer having from 6 to 12 carbon atoms, selected from the group consisting of dialkyl aminoalkyl methacrylamide, dialkyl dialkenyl ammonium halide and a dialkylamino alkyl methacrylate or acrylate and between about 0–5 weight % stearyl methacrylate.

4. The hair conditioning polymer of claim 3 wherein said ammonium derivative monomer is dimethylamino ethyl methacrylate.

5. The hair conditioning polymer of claim 4 wherein the weight ratio of N-vinyl-ε-caprolactam to vinyl pyrrolidone to dimethylamino ethyl methacrylate is about 69–73:22–26:3–6.

6. The hair conditioning polymer of claim 3 wherein the terpolymer also contains of stearyl methacrylate.

7. The hair conditioning polymer of claim 3 which has a K value of at least 30.

8. The hair conditioning polymer of claim 3 which has a K value of between about 35 and about 50.

9. The hair conditioning polymer of claim 5 wherein about 3% by weight of the N-vinyl-ε-caprolactam is replaced with stearyl methacrylate.

10. The hair conditioning polymer of claim 3 wherein the terpolymer is quaternized.

* * * * *